US012352669B2

(12) United States Patent
Royer

(10) Patent No.: US 12,352,669 B2
(45) Date of Patent: *Jul. 8, 2025

(54) SOIL PROBE ASSEMBLY HAVING A MULTIFACETED PROBE WHEEL

(71) Applicant: Jeffrey L. Royer, Neola, IA (US)

(72) Inventor: Jeffrey L. Royer, Neola, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/429,977

(22) Filed: Feb. 1, 2024

(65) Prior Publication Data

US 2024/0344935 A1 Oct. 17, 2024

Related U.S. Application Data

(63) Continuation of application No. 17/518,305, filed on Nov. 3, 2021, now Pat. No. 11,921,016.

(51) Int. Cl.
| | |
|---|---|
| G01N 1/08 | (2006.01) |
| G01N 33/24 | (2006.01) |
| A01B 29/06 | (2006.01) |
| A01B 35/16 | (2006.01) |
| A01B 35/28 | (2006.01) |
| A01B 35/32 | (2006.01) |
| A01B 76/00 | (2006.01) |
| A01B 79/00 | (2006.01) |

(52) U.S. Cl.
CPC ............... *G01N 1/08* (2013.01); *G01N 33/24* (2013.01); *A01B 29/06* (2013.01); *A01B 35/16* (2013.01); *A01B 35/28* (2013.01); *A01B 35/32* (2013.01); *A01B 76/00* (2013.01); *A01B 79/00* (2013.01); *G01N 33/245* (2024.05)

(58) Field of Classification Search
CPC .... G01N 1/08; G01N 33/24; G01N 2033/245; A01B 29/06; A01B 35/16; A01B 35/28; A01B 35/32; A01B 76/00; A01B 79/00
See application file for complete search history.

(56) References Cited

U.S. PATENT DOCUMENTS

| | | |
|---|---|---|
| RE30,901 E | 4/1982 | Boxrud |
| 6,766,865 B1 | 7/2004 | Dagel et al. |
| 8,613,234 B1 | 12/2013 | Harrell |
| 9,200,492 B2 | 12/2015 | McGraw |
| 9,534,464 B1 | 1/2017 | Kelley et al. |
| 10,145,192 B1 | 12/2018 | Kelley et al. |
| 2010/0028080 A1 | 2/2010 | Wallace |

FOREIGN PATENT DOCUMENTS

CA 2975458 A1 2/2018

*Primary Examiner* — Benjamin R Schmitt
(74) *Attorney, Agent, or Firm* — Ryan T. Grace; Advent, LLP

(57) ABSTRACT

A soil probe assembly includes a frame member and a wheel rotatably coupled to the frame member. The wheel includes one or more soil probes that, as the wheel rotates against the earth, the weight of the soil probe assembly drives the soil probes into the earth. The wheel is configured to have at least two planar edges such that, as the wheel rolls onto one of the at least two planar edges, a slamming effect occurs due to the planar edge impacting against the ground, thus causing a soil sample to eject from a soil probe located across the wheel from the ground. The ejected soil sample is collected by a collection hamper. The assembly includes a funnel and a carousel such that the funnel is configured to receive and direct the ejected soil sample to the collection hamper, wherein the collection hamper is coupled to the carousel.

6 Claims, 12 Drawing Sheets

SOIL PROBE ASSEMBLY HAVING A MULTIFACETED PROBE WHEEL

BACKGROUND

Soil samplers or soil probes are commonly used to extract a soil core or plug from the ground for analysis. Many soil sampling devices have been previously provided with those devices ranging from hand-held probes to large soil sampling machines.

BRIEF DESCRIPTION OF THE DRAWINGS

The Detailed Description is described with reference to the accompanying figures. The use of the same reference numbers in different instances in the description and the figures may indicate similar or identical items. The drawings are not necessarily to scale.

DETAILED DESCRIPTION

Figure 1:
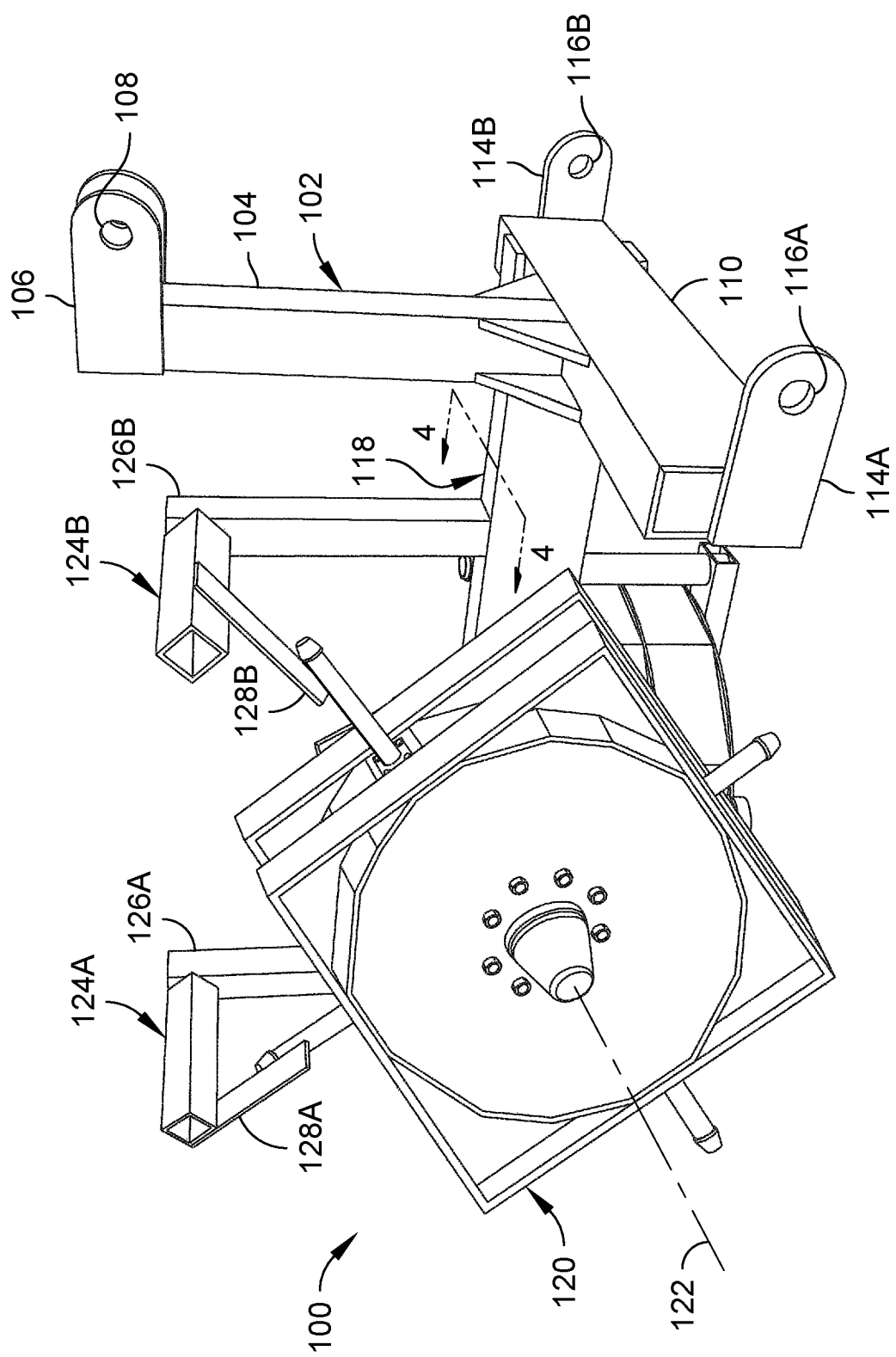
FIG. 1 is a perspective view illustrating a soil probe assembly including a wheel and a set of carousels in accordance with an example embodiment of the present disclosure.

While the embodiments of the present application are susceptible to various modifications and alternative forms, specific embodiments thereof have been shown by way of example in the drawings and are herein described in detail. However, it should be understood that the description herein of specific embodiments is not intended to limit the application to the particular embodiment disclosed, but on the contrary, the intention is to cover all modification, equivalents, and alternatives falling within the spirit and scope of the present application as defined by the appended claims. It should be noted that the articles "a," "an," and "the," as used in this specification, include plural referents unless the content clearly dictates otherwise. Additional features and functions are illustrated and discussed below.

Overview

Within the practice of farming, farmers monitor soil quality of a worked field by collecting soil samples from the field and testing the soil samples for various characteristics, such as nutrient content and pH levels, in order to determine whether the overall soil of the field is suitable for a particular crop or to determine what crop is suitable based on the determined characteristics of the soil.

Various soil probe devices have been developed to obtain soil samples. For example, some soil probe devices are simple hand-operated devices that obtain a single soil sample. However, a hand-operated soil probe may prove to be too labor-intensive and untimely for a user when it is desired to test multiple locations. Alternatively, some soil probe devices are hydraulically or electrically actuated to drive the soil probe into the earth. However, these hydraulic and electrical actuated soil probe devices require additional costly equipment such as hydraulic pumps, hydraulic control systems, and high-torque electric motors, which can be difficult to use, maintain, and repair. Furthermore, when testing multiple regions of a field or across multiple fields, these soil probe devices generally do not provide a system for separating soil samples in order to prevent soils samples from mixing with other soil samples from different test regions, thus placing the burden on the user to separate the soil samples by hand.

Accordingly, the present disclosure is directed to a soil probe assembly that includes a frame member and a wheel rotatably coupled to the frame member. The wheel includes one or more soil probes that, as the wheel rotates against the earth, the weight of the soil probe assembly drives the soil probes into the earth, thereby removing the need for costly equipment to apply a force to drive soil probes into the ground. To collect a soil sample from a probe on the wheel, the wheel is configured to have at least two planar edges such that, when the wheel rolls onto one of the at least two planar edges, a "slamming" effect occurs due to the planar edge of the wheel impacting against the ground, thus causing a soil sample to eject from a soil probe located across the wheel opposite from the planar edge that impacted the ground. The ejected soil sample is then collected by a hamper that is coupled to the frame member. The soil probe assembly further includes a funnel and a carousel such that the funnel is configured to receive and direct the ejected soil sample to the collection hamper, wherein the collection hamper is coupled to the carousel.

In embodiments, the soil probe assembly has a hitch receiver coupled to the frame member, such as a 3-point hitch receiver, that is configured to couple to a vehicle, such as a tractor or a passenger vehicle, so as to permit towing by the vehicle.

In further embodiments, the soil probe assembly is coupled to a trailer configured to house the soil probe assembly. The trailer is further configured couple to a vehicle and to permit the soil probe assembly to operate while housed by the trailer.

In an embodiment, the soil probe assembly has a carousel that includes one or more collection hampers such that a collection hamper among the one or more collection hampers may receive the ejected soil sample, thereby permitting selective separation of the soil samples among the one or more collection hampers. The carousel is configured to be selectively positioned about an axis, wherein a selected position of the carousel determines which collection hamper among the one or more collection hampers receives the ejected soil sample. Optionally, the carousel includes a bypass that, when selected, allows ejected soil samples to pass through the bypass without collection and therefore returned to the ground.

In a further embodiment, the carousel is coupled to a support arm that is pivotably coupled to a frame member of the soil probe assembly such as to allow a user to pivot the carousel away from the frame member for user access to the one or more collection hampers.

In a further embodiment, the soil probe assembly includes a second carousel having one or more collection hampers such that, when the bypass of a first carousel is selected, ejected soil samples may pass through the bypass and be received by a collection hamper among the one or more collection hampers located on the second carousel, thus allowing additional storage and/or separation of collected soil samples. Optionally, the second carousel includes a bypass that, when the bypass of the first carousel and the bypass of the second carousel are selected, allows ejected soil samples to pass through the bypasses of the first and second carousels without collection and therefore returned to the ground.

In an embodiment, the soil probe assembly includes an actuator-driven funnel shield that is configured to selectively cover a collection opening of the funnel, thereby prohibiting ejected soil samples from being collected in a collection hamper.

In another embodiment, the soil probe assembly includes one or more probe brushes configured to scrape debris off the one or more soil probes as the wheel rotates so as to maintain consistent ground penetration by the one or more soil probes.

Example Implementations

Generally referring to FIGS. 1-2, 4-5, and 7-8, a soil probe assembly 100 (hereinafter referred to as "assembly 100") is described in accordance with an embodiment of the present disclosure. In general, assembly 100 includes frame member 118, wheel 120, funnel 130, and at least one collection hamper (e.g., collection hamper 204A). In general, frame member 118 is coupled to a hitch receiver configured to receive a hitch, wherein a hitch is any coupling device attached to a vehicle (e.g., a tractor, passenger vehicle, etc.) or trailer that is configured to tow a load. For example, a hitch may include, but is not limited to, a 3-point hitch, a 5th wheel hitch, a gooseneck hitch, a weight-distribution hitch, a pintle hitch, etc.

In an embodiment, frame member 118 is coupled to hitch receiver 102, wherein hitch receiver 102 is a 3-point hitch receiver configured to couple with a 3-point hitch of a vehicle. Hitch receiver 102 includes first member 104 coupled to second member 110. Furthermore, first member 104 is coupled to hitch receiver bracket 106, and second member 110 is coupled to hitch receiver brackets 114A and 114B. Hitch receiver bracket 106, 114A, and 114B have respective apertures 108, 116A, and 116B configured to couple to a hitch using a set of pins. For example, in reference to FIG. 7, each hitch receiver bracket is coupled to a respective set of linkages of a 3-point hitch using a respective set of pins. In this figure, hitch receiver bracket 106 is coupled to linkage 226 using pin 228A, and hitch receiver bracket 114B is coupled to linkage 227 using pin 228B (hitch receiver bracket 114A is obscured from view; however, hitch receiver bracket 114A is likewise coupled to a respective linkage using a respective pin in the same form and fashion as hitch receiver bracket 114B is coupled to linkage 227 using pin 228B). While the figures illustrate a single example of a 3-point hitch receiver, it should be appreciated that hitch receiver 102 may come in a variety of configurations that include brackets 108, 116A, and 116B (e.g., an A-frame 3-point hitch receiver). Furthermore, it should be appreciated that hitch receiver 102 is not limited to 3-point hitch receivers and is permitted to be any hitch receiver that is configured to couple to a corresponding hitch known in the art of hitches.

In an embodiment, frame member 118 is pivotably coupled to hitch receiver 102. In reference to FIG. 5, frame member 118 is pivotably coupled to hitch receiver 102 according to hinge 206. Hinge 206 includes pin 207 that defines axis 208, wherein frame member 118 and hitch receiver 102 pivot with respect to axis 208. In a further embodiment, frame member 118 includes one or more angle members (e.g., angle member 210) located proximate to hinge 206 and transverse to axis 208, wherein the one or more angle members are configured to obstruct frame member 118 and hitch receiver 102 from pivoting beyond an angle defined by the one or more angle members.

In general, wheel 120 is coupled to frame member 118, wherein wheel 120 is configured to rotate with respect to axis 122. In an embodiment, assembly 100 includes axle 146 which couples wheel 120 to frame member 118. Axle 146 includes axle member 148, spindle 150, and hub 152. Axle member 148 is a support structure that is coupled to frame member 118 and spindle 150. Hub 152 is rotatably coupled to spindle 150 wherein hub 152 is configured to rotate with respect to axis 122 that passes longitudinally through spindle 150. Hub 152 includes one or more studs (e.g., stud 152) arranged in a circular array about axis 122 for receiving a respective one or more apertures (e.g., aperture 160) that are defined by wheel 120. Wheel 120 is coupled to hub 152 according to one or more fasteners (e.g., fastener 162) that respectively couple to the one or more studs on hub 152.

While the figures illustrate a single example of a configuration that permits wheel 120 to rotate with respect to axis 122, it should be appreciated that alternate configurations for permitting wheel 120 to rotate about axis 122 are contemplated. For example, assembly 100 may include an axle that defines axis 122, wherein the axis is coupled to wheel 120 and is further rotatably coupled to frame member 118, wherein the axle and wheel 120 together rotate about axis 122 with respect to frame member 118.

Figure 2:
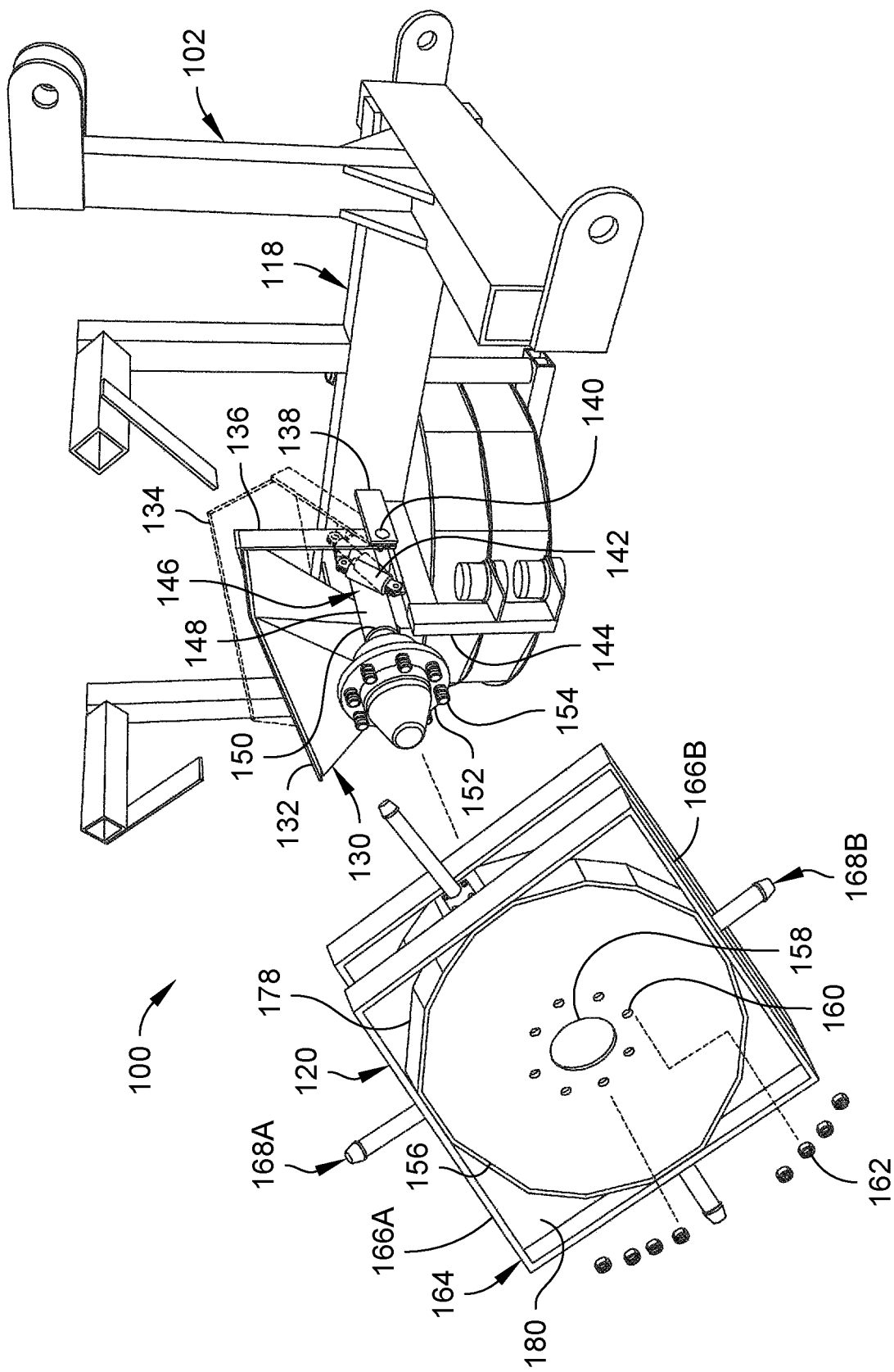
FIG. 2 is an exploded view of the soil probe assembly illustrated in FIG. 1.
Figure 3:
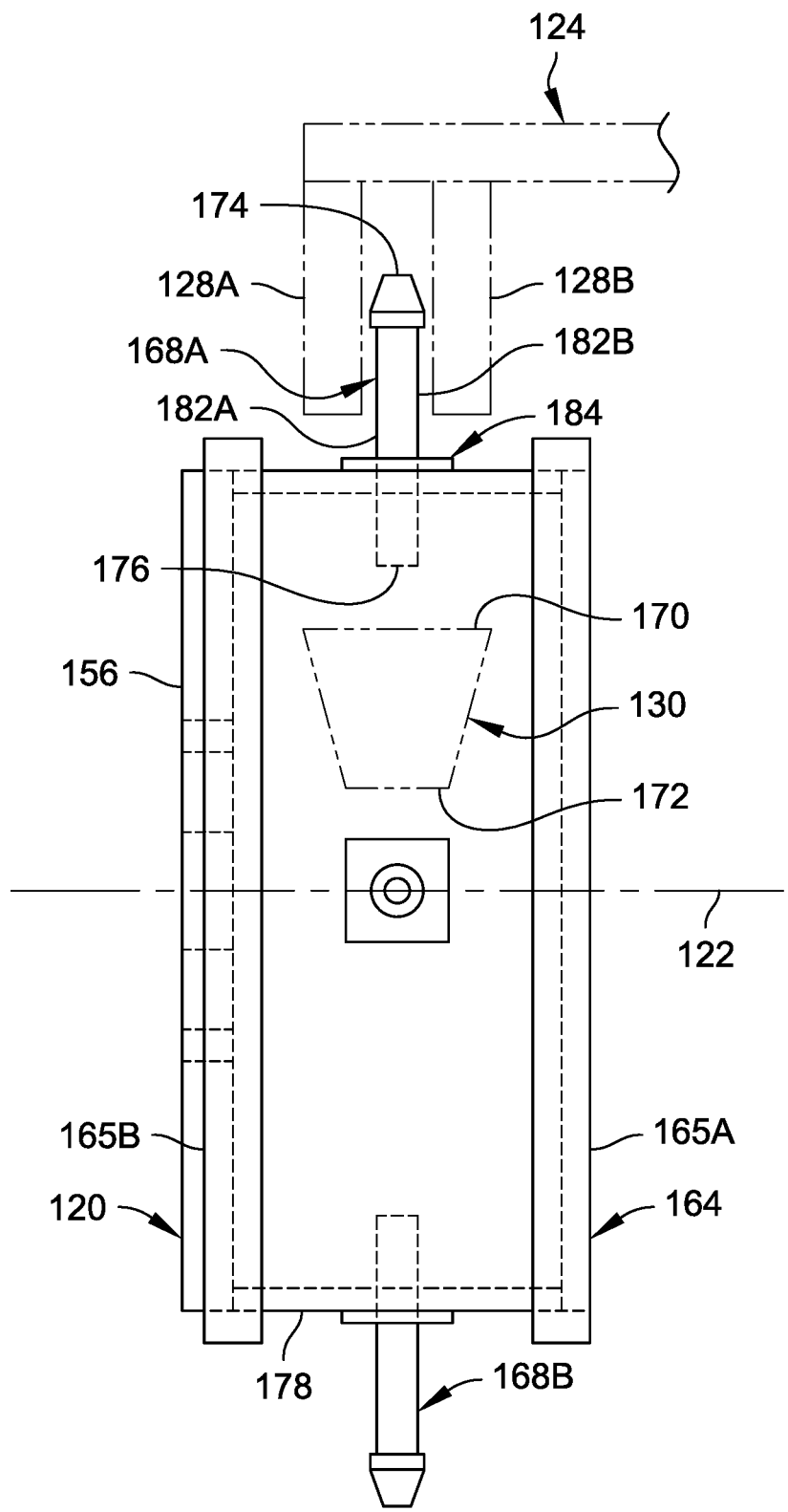
FIG. 3 is an end view illustrating a wheel for a soil probe assembly, such as the soil probe assembly illustrated in FIG. 1, in accordance with an example embodiment of the present disclosure.

Now referring to FIG. 2 and FIG. 3, wheel 120 is described in accordance with an example embodiment of the present disclosure. In general, wheel 120 includes wheel hub 156, rim 164 that is coupled to wheel hub 156, and one or more tubular soil probes (e.g., soil probe 168A and 168B) that is coupled to rim 164.

In an embodiment, wheel hub 156 includes hub aperture 168B and one or more apertures (e.g., aperture 160), wherein hub aperture 168B and aperture 160 are defined by wheel hub 156. The one or more apertures may be arranged in a circular array centered about axis 122. Hub aperture 168 is configured to receive a portion of hub 152 for centering wheel 120 relative to axis 122. The one or more apertures are configured to receive one or more studs (e.g., stud 154) for coupling wheel 120 to hub 152.

Rim 164 is a rim of wheel 120 that is periodically in contact with the ground as wheel 120 rotates to collect soil samples. In general, rim 164 has at least two planar edges, wherein the two planar edges are located opposite from each other across wheel 120. For example, wheel 120 may have rim 164 that has two opposing planar edges (e.g., planar edge 166A and 166B) and two curved edges that each periodically make contact with the ground as wheel 120 rotates about axis 122 while assembly 100 is collecting soil samples. In an embodiment, rim 164 may include one or more rim members that are planarly parallel to each other, wherein the one or more rim members define a planar edge. As shown in FIG. 3, rim members 165A and 165B are planarly parallel to each other that define a planar edge such as planar edge 166B.

In an embodiment, inner rim member 178 inscribes wheel hub 156 and couples rim 164 to wheel hub 156. In further embodiments, rim support member 180 couples rim 164 to inner rim member 178, wherein rim support member 180 radially extends from inner rim member 178 relative to axis 122 and can be, but is not limited to, a planar member or a plurality of spokes. As shown in FIG. 2, rim support member 180 is a planar member that couples inner rim member 178 to rim 164. In another embodiment, inner rim member 178 defines rim 164 and includes at least two planar edges.

In general, at least one tubular soil probe is coupled to at least one of the at least two planar edges. In an embodiment, wheel 120 has opposing planar edges 166A and 166B wherein soil probe 168A is coupled to planar edge 166A. In a further embodiment, a soil probe is coupled to each planar edge of rim 164. For example, in FIG. 2, rim 164 has four planar edges with a soil probe coupled to each planar edge (e.g., soil probe 168A is coupled to planar edge 166A, soil probe 168B is coupled to planar edge 166B, etc.).

Figure 10:
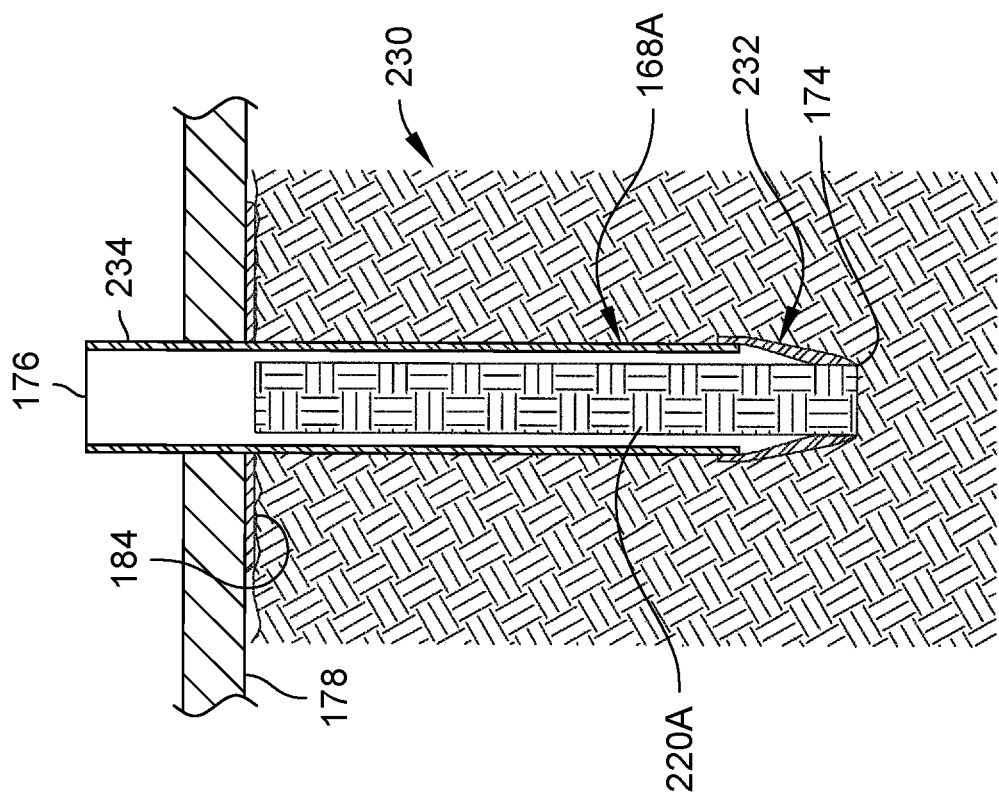
FIG. 10 is a cross-section view illustrating a soil probe for the soil probe assembly of FIG. 1, wherein the soil probe is submerged in the ground to extract a soil sample.
Figure 9:
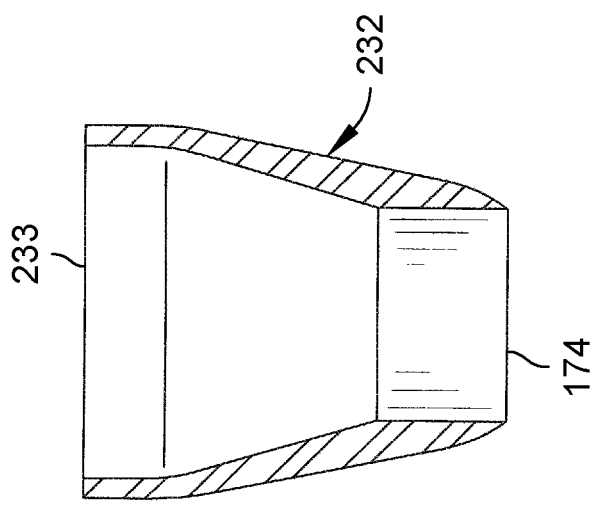
FIG. 9 is a cross-section view illustrating a probe tip of a soil probe utilized for a soil probe assembly, such as the soil probe assembly of FIG. 1, in accordance with an example embodiment of the present disclosure.

An example embodiment of a soil probe is described in reference to FIGS. 3, 9, and 10. As each soil probe on wheel 120 are identical, only probe 168A will be described in detail. In general, soil probe 168A is a tubular soil probe having extraction opening 174 and ejection opening 176, wherein extraction opening 174 and ejection opening 176 are in fluid communication with each other and are located on opposing ends of soil probe 168A. Soil probe 168A is oriented on wheel 120 such that soil probe 168A extends radially with respect to axis 122 such that extraction opening 174 is distal from axis 122.

In an embodiment, soil probe 168A is configured to receive a soil sample from the ground at extraction opening 174 and is configured to release the soil sample from ejection opening 176. For example, in reference to FIG. 10, soil probe 168A receives soil sample 220A by penetrating ground 230. In this example, soil probe 168 is coupled to inner rim member 178 and mounting bracket 184, wherein inner rim member 178 defines a portion of rim 164 and a portion of a planar edge of wheel 120. Soil probe 168 is configured to pass through inner rim 178 and mounting bracket 184 such that extraction opening 174 is in communication with an exterior of wheel 120 and ejection opening 174 is in communication with an interior of wheel 120.

Soil probe 168A includes tube 234 coupled with probe tip 234. Probe tip 232 has extraction opening 174 and opening 233, wherein extraction opening 174 has a smaller diameter than opening 233 such that soil sample 220A will have a diameter that is less than the diameter of opening 233. Opening 233 is configured to receive tube 234, wherein the inner diameter of tube 234 is larger than extraction opening 174. As soil probe 168A is removed from ground 230 as wheel 120 rotates, soil sample 230A remains lodged within extraction opening 174.

Figure 7:
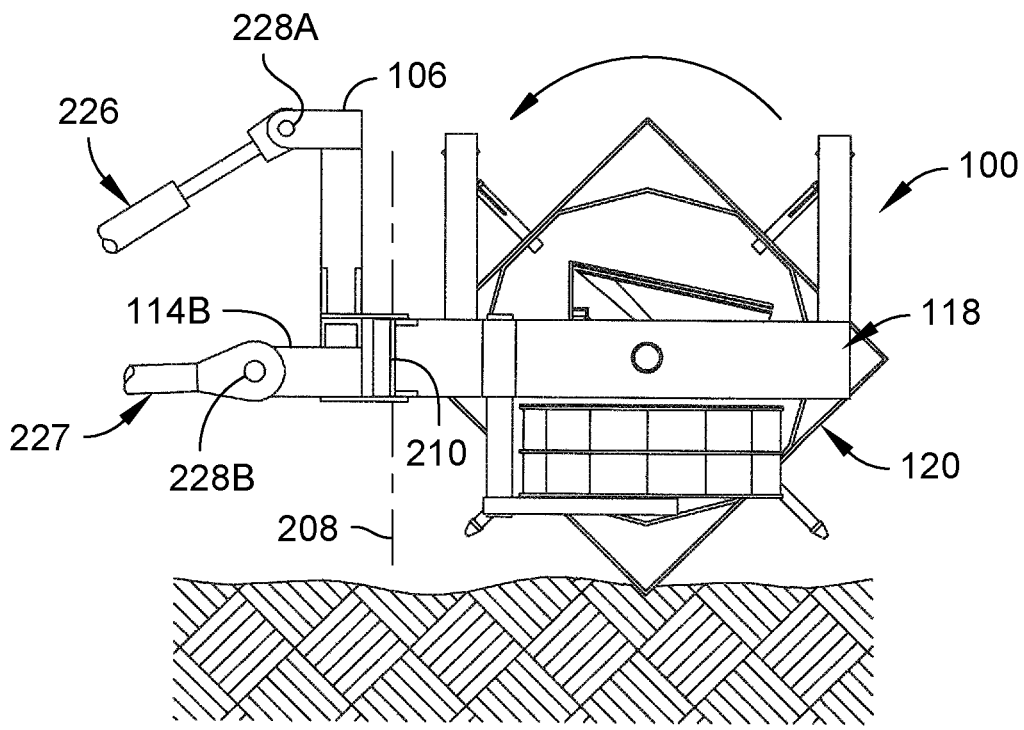
FIG. 7 is a side view of the soil probe assembly illustrated in FIG. 1, wherein the wheel is in a first orientation.
Figure 8:
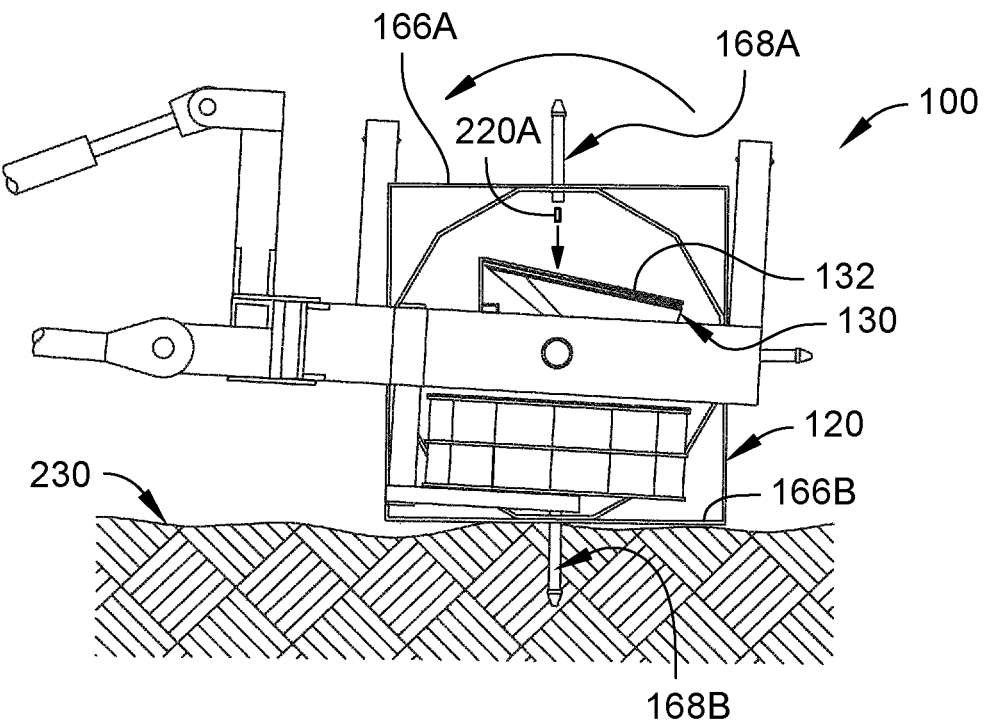
FIG. 8 is a side view of the soil probe assembly illustrated in FIG. 1, wherein the wheel is in a second orientation.

To eject soil sample 220A from soil probe 168A, wheel 120 undergoes a slamming effect which dislodges soil sample 220A from soil probe 168A, wherein soil sample 220A exits soil probe 168A from ejection opening 176. For example, in reference to FIGS. 7 and 8, as wheel 120 rotates from a first orientation as illustrated in FIG. 7 to a second orientation as illustrated in FIG. 8 wherein planar edge 166B slams (i.e., impacts) against ground 230. In this example, at an instant before impact, soil probe 168A is located opposite to ground 230 across wheel 120, wherein soil sample 220A is lodged within soil probe 168A. When planar edge 166B impacts against ground 230, the impact causes soil sample 220A to release from soil probe 168A and subsequently exits soil probe 168A from ejection opening 176 towards the interior of wheel 120.

In an embodiment, assembly 100 includes funnel 130 having collection opening 170 and delivery opening 172, wherein collection opening 170 and delivery opening 172 are in fluid communication with each other, and wherein collection opening 170 is located proximate to ejection opening 176 of a soil probe during the instant the soil probe releases soil sample 220A as a result of the slamming effect. For example, in reference to FIGS. 3 and 8, when wheel 120 impacts with ground 230 and soil sample 220A is released from soil probe 168A, funnel 130 is located proximate to ejection opening 176 of soil probe 168A so as to receive the released soil sample. In an embodiment, bracket 131 couples funnel 130 to frame member 118, as is shown in FIG. 4.

Figure 4:
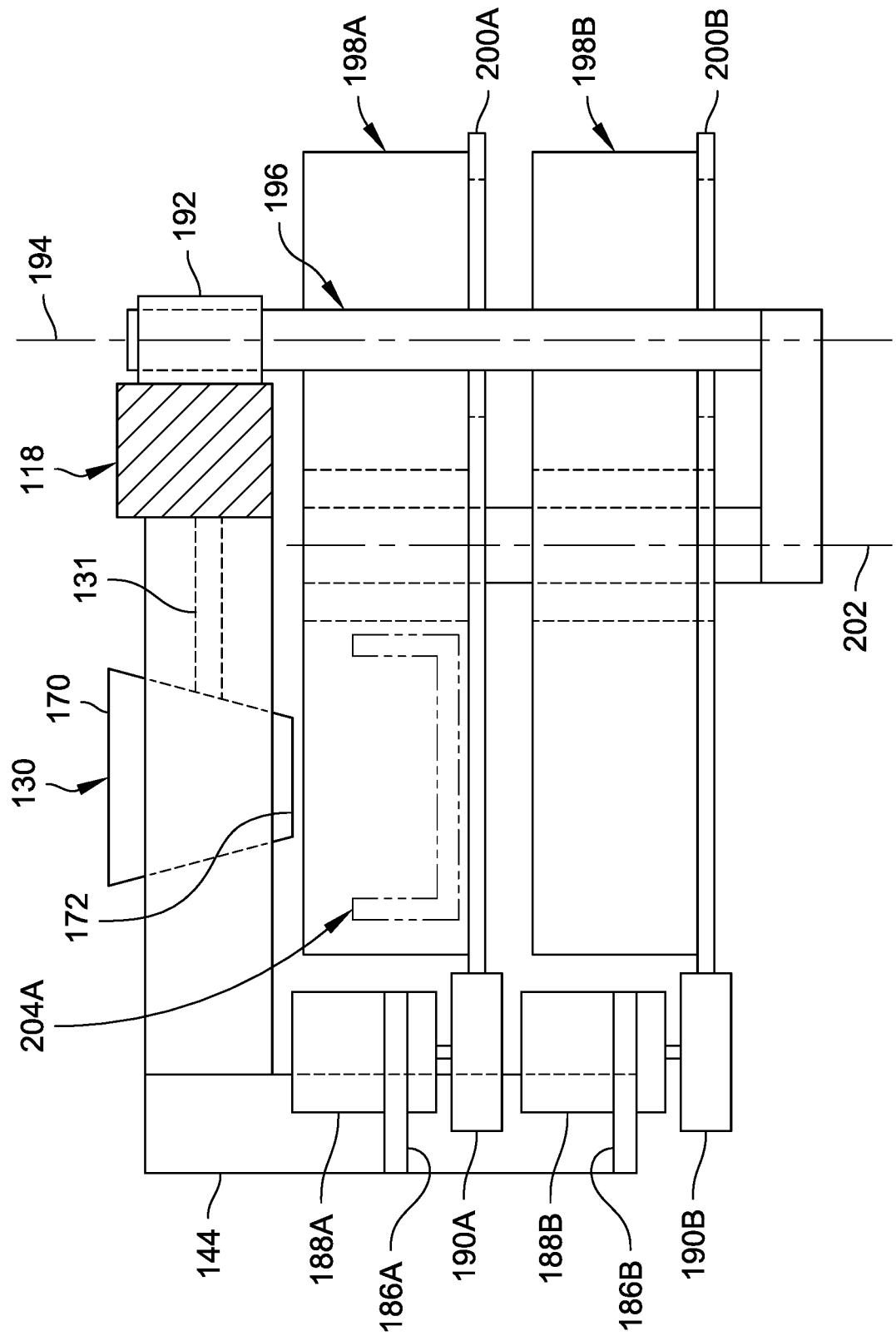
FIG. 4 is a partial section view 4-4 of the soil probe assembly illustrated in FIG. 1.

In an embodiment, assembly 100 includes collection hamper 204A that is configured to receive soil sample 220A released by funnel 130 from delivery opening 172, as shown in FIG. 4. In general, collection hamper 204A is a hamper for collecting soils samples. For example, collection hamper 204A can be cardboard box, a basket, or any other container capable of receiving and storing soil samples. In an embodiment, collection hamper 204 is connectable to the frame member 118.

In an embodiment, assembly 100 includes a support arm pivotably coupled to frame member 118, a carousel rotatably coupled to the support arm wherein the carousel is configured to be selectively positioned about an axis of the carousel, and wherein the collection hamper is configured to selectively receive the soil sample released by the funnel based on the selected position of the carousel.

Figure 5:
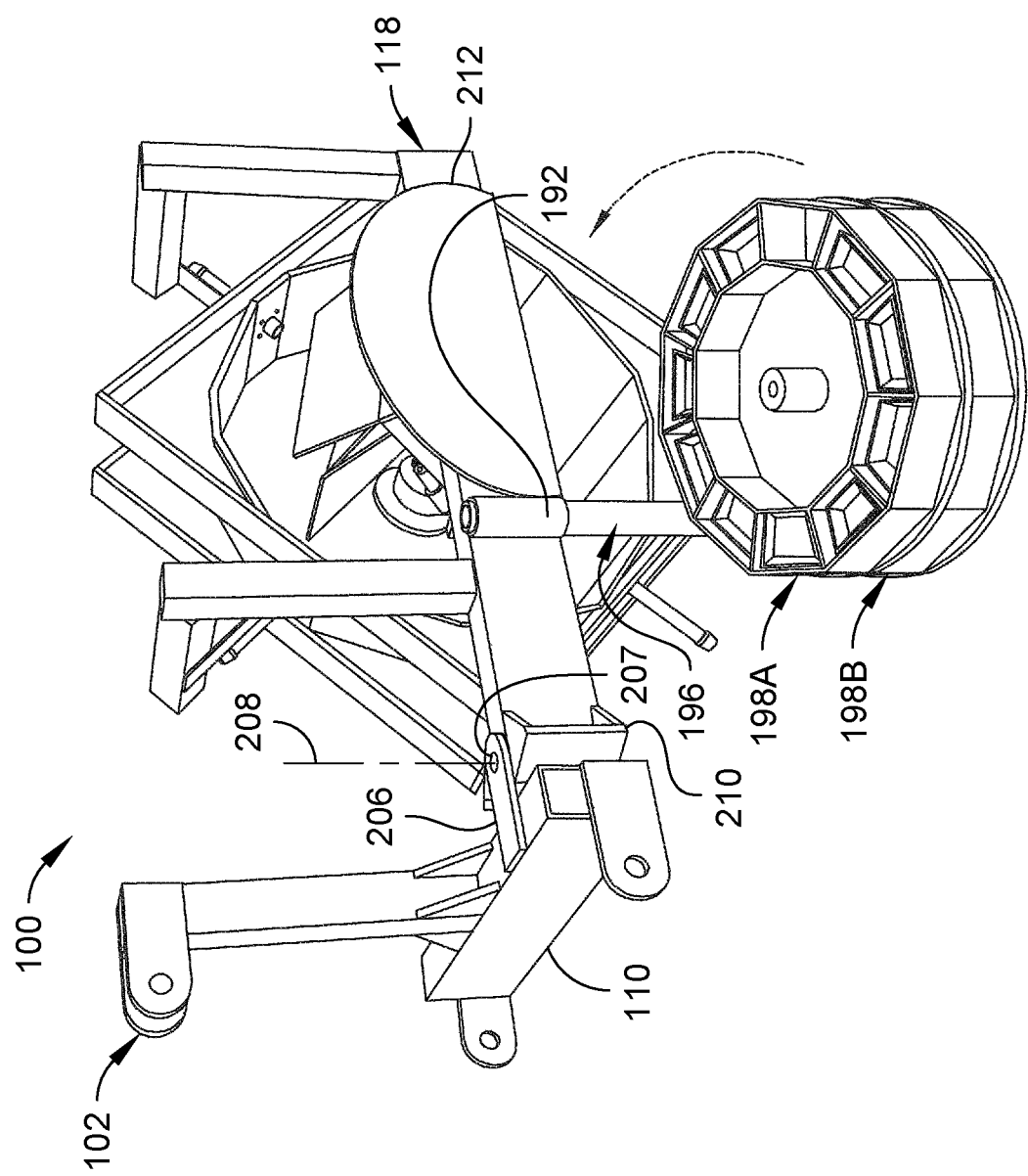
FIG. 5 is another perspective view of the soil probe assembly illustrated in FIG. 1, wherein the set of carousels are positioned in a distal orientation to permit user access.
Figure 6:
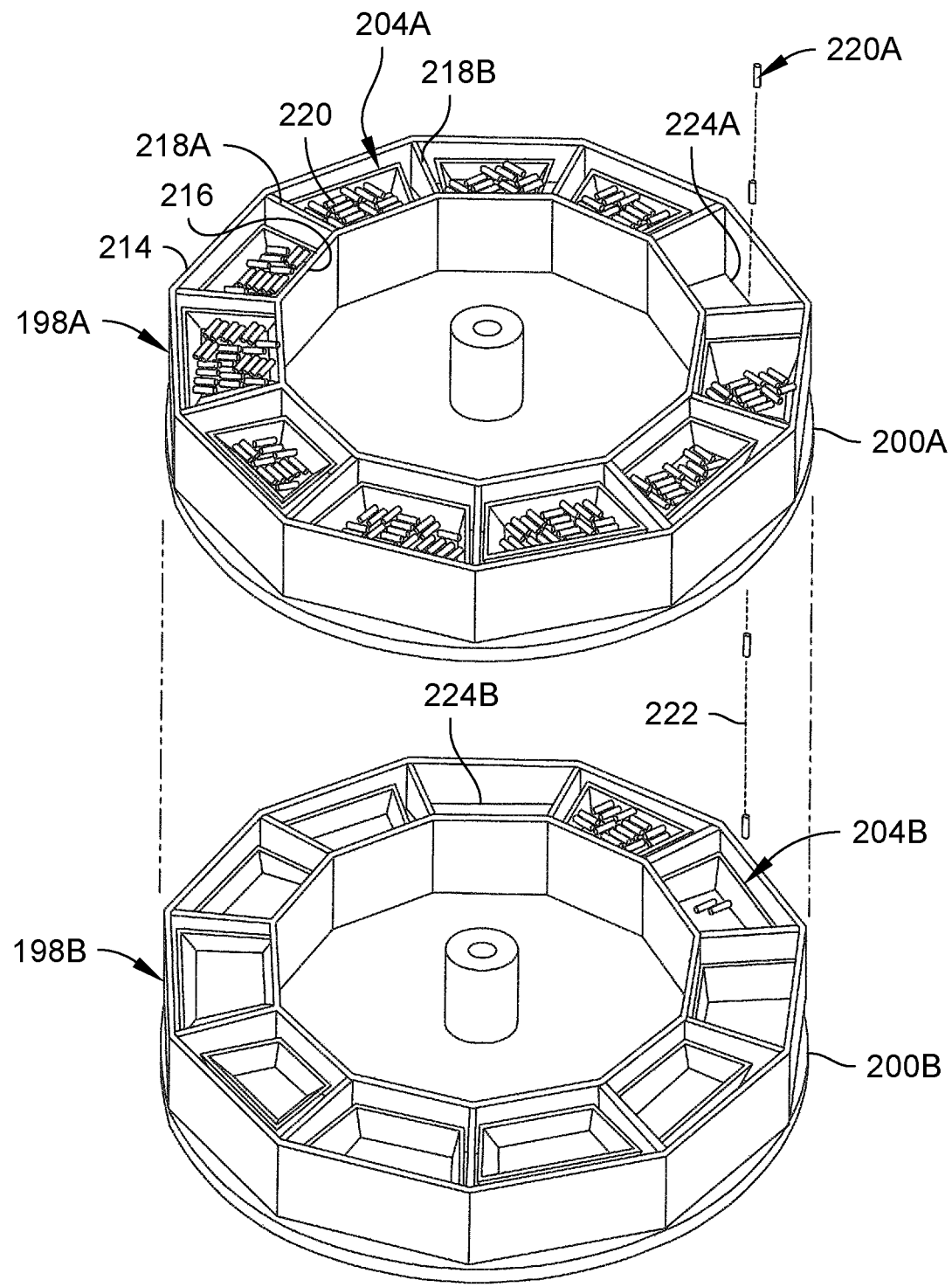
FIG. 6 is a perspective view illustrating a first carousel and a second carousel for a soil probe assembly, such as the soil probe assembly illustrated in FIG. 1, in accordance with an example embodiment of the present disclosure.

In reference to FIGS. 4-6 example embodiments of the support arm, the carousel, and the collection hamper are discussed in further detail. In an embodiment, hinge 192 couples support arm 196 to frame 118 and is configured to permit support arm 196 to pivot about axis 194, wherein axis 194 is defined by hinge 192. As shown in FIG. 5, support arm 196 is permitted to pivot according to hinge 192 in order to permit a user to access one or more collection hampers stored on one or more carousels that are rotatably coupled to support arm 196.

In reference to FIGS. 4 and 6, an example embodiment of a set of carousels is depicted and described. In general, a carousel is a structural platform that is configured to selectively position about an axis, wherein the carousel includes one or more collection hampers that are connectable to the carousel. In an embodiment, carousel 198A is rotatably coupled to support arm 196, wherein carousel 198A is configured to rotate about axis 202 that is defined by support arm 196. Carousel 198A may include platform 200A, outer wall 214, inner wall 216, and a plurality of partitions (e.g., partitions 218A and 218B), wherein outer wall 214, inner wall 216, and the plurality of partitions are coupled to platform 200A, and the plurality of partitions each couple to outer wall 214 and inner wall 216.

One or more hampers are connectable to carousel 198A. In general, the one or more collection hampers (e.g., collection hamper 204A) are configured to receive a soil sample (e.g., soil sample 220A) released by funnel 130 based on a selected position of the carousel. In an embodiment, the one or more collection hampers are connectable to carousel 198A by being contained through contact communication between outer wall 214, inner wall 216, and a plurality of partitions. For example, as shown in FIG. 6, collection hamper 204A is contained through contact communication with platform 200A and located between outer wall 214, inner wall 216, and partitions 218A and 218B. In a further embodiment, a plurality of collection hampers, including collection hamper 204A, are arranged in a circular array about axis 202, wherein any single collection hamper among the plurality of collection hampers is configured to receive soil sample 220A based on a selected position of the carousel. As shown in FIG. 6, soil samples 220 are collected in the one or more collection hampers.

In an embodiment, carousel 198A includes bypass 224A defined by the carousel. In an embodiment, bypass 224A is defined by platform 200A. In general, bypass 224A is configured to selectively permit soil samples to pass through bypass 224A without capture by carousel 198A based on a selected position of the carousel. For example, in reference to FIG. 6, when bypass 224A is selected (i.e., carousel 198A is rotated to a position such that bypass 224A is positioned to receive soil sample 220A from delivery opening 172), then soil sample 220A, traversing trajectory 222, is permitted to pass through bypass 224A without collection by carousel 198A.

In a further embodiment, assembly 100 includes a second carousel rotatably coupled to the support arm, wherein the second carousel is configured to selectively position about the axis of the carousel, and wherein the second carousel is located beneath carousel 198A. For example, in reference to FIGS. 4 and 6, assembly 100 includes a carousel 198B, wherein carousel 198B is similar function as carousel 198A, wherein carousel 198B is rotatably coupled to support arm 196, wherein carousel 198A is configured to selectively position about axis 202. Carousel 198B is located beneath carousel 198A such that, when bypass 224A of carousel 198A is selected, then soil sample 220A, traversing trajectory 222, must pass through bypass 224A before reaching carousel 198B.

In an embodiment, carousel 198B includes one or more collection hampers (e.g., collection hamper 204B) connectable to carousel 198B, wherein the one or more collection hampers are configured to receive a soil sample (e.g., soil sample 220A) that pass through bypass 224A of carousel 198A, wherein any single collection hamper among the one or more collection hampers is configured to receive the soil sample based on a selected position of carouse 198B. For example, in reference to FIG. 6, when bypass 224A of carousel 198A is selected, then soil sample 220A, traversing trajectory 222, passes through bypass 224A and is collected by collection hamper 204B. Although FIG. 6 illustrates only a first and a second carousel, it should be appreciated that assembly 100 may include any plurality of carousels, each similar to each other in function.

In an embodiment, carousel 198B includes bypass 224B defined by carousel 198B. In an embodiment, bypass 224B is defined by platform 200B. In general, bypass 224B is configured to selectively permit soil samples to pass through bypass 224B without capture by carousel 198B based on a selected position of carousel 198B. For example, when bypass 224A of carousel 198A and bypass 224B of carousel 198B are both selected, then soil sample 220A is permitted to pass through both bypasses 224A 224B without collection by carousels 198A and 198B.

In an embodiment, the one or more carousels are selectively positioned about axis 202 using one or more respective motors that drive the one or more carousels. In a further embodiment, each motor is coupled with a drive wheel that transfers a torque provided by the motor to a respective carousel, wherein the drive wheel is in contact communication with the respective carousel. For example, with respect to FIG. 4, assembly 100 includes arm member 144 coupled to frame member 118, motor mounting brackets 186A and 186B coupled to arm member 144, and motors 188A and 188B respectively coupled to mounting brackets 186A and 186B. Furthermore, drive wheels 190A and 190B are respectively coupled to motors 188A and 188B, wherein drive wheels 190A and 190B are in contact communication with respective carousels 198A and 198B such that torques supplied by respective motors 188A and 188B transfer to carousels 198A and 198B, thus causing carousels 198A and 198B to rotate based upon the respective motors. Motors 188A and 188B can be, but are not limited to, an electric motor, such as a stepper motor, or a hydraulic motor. In one embodiment, drive wheels 190A and 190B are friction wheels. In another embodiment, drive wheels 190A and 190B are teethed wheels (i.e., a gear), wherein each respective carousel is further configured to receive the teethed wheels.

In an embodiment, assembly 100 may include a carousel lid, such as lid 212 as shown in FIG. 5, wherein lid 212 is pivotably coupled to frame member 118 and is configured to selectively cover at least carousel 198A.

In one embodiment, assembly 100 includes one or more probe brushes configured to scrape debris off the one or more soil probes as the wheel rotates so as to maintain consistent ground penetration by the one or more soil probes. With respect to FIG. 3, an example embodiment depicts brush arm 124 having probe brushes 128A and 128B, wherein probe brush 128A and 128B are configured to scrape debris off a soil probe as wheel 120 rotates. For example, in FIG. 3, probe brush 128A is located proximate to portion 182A of soil probe 168A, and probe brush 128B is located proximate to portion 182B of soil probe 168A, wherein portions 182A and 182B are opposing sides of probe 168A. In this configuration, as soil probe 168A rotates with wheel 120 and passes probe brushes 128A and 128B, probe brushes 128A and 128B scrape debris off soil probe 168A. In an embodiment, brush arm 124 is coupled to frame member 118.

In another embodiment, probe brushes 128A and 128B are coupled to a respective brush arm that is coupled to frame 118. For example, in FIG. 1, brush arm 124A includes probe brush 128A and support member 126A, wherein support member 126A couples probe brush to frame member 118. Furthermore, brush arm 124B includes probe brush 128B and support member 126B, wherein support member 126B couples probe brush to frame member 118.

In an embodiment, assembly 100 includes a funnel shield, wherein the funnel shield is configured to selectively cover the collection opening of the funnel, thereby prohibiting soil samples from entering the funnel. For example, with respect to FIGS. 2 and 8, funnel shield 132 is configured to selectively cover collection opening 170 of funnel 130, thereby prohibiting soil sample 220A released from soil probe 168A from entering funnel 130. Funnel shield 132 is coupled to arm member 136, wherein arm member 136 is pivotably coupled to mounting bracket 138 according to hinge 140, wherein mounting bracket 138 is also coupled to frame member 118, and wherein arm member 136 is coupled to actuator 142 that selectively positions funnel shield 132 to cover funnel 130. In this example, actuator 142 is a linear actuator that is coupled to arm member 136 and arm member 144. To permit soil samples to enter funnel 130, actuator 142 positions funnel shield 132 to position 134.

Figure 11:
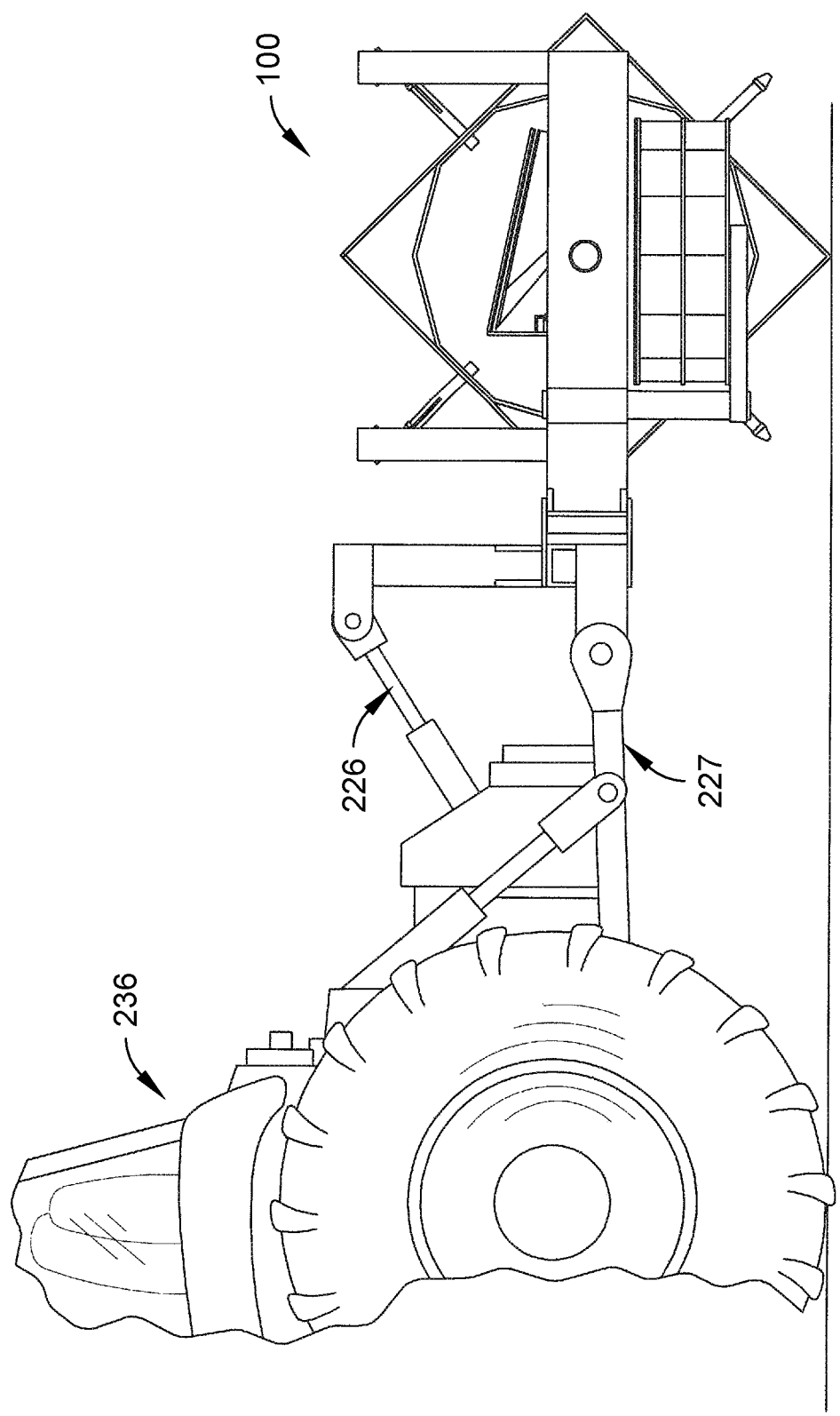
FIG. 11 is a side view illustrating the soil probe assembly of FIG. 1 coupled to a tractor.
Figure 12:
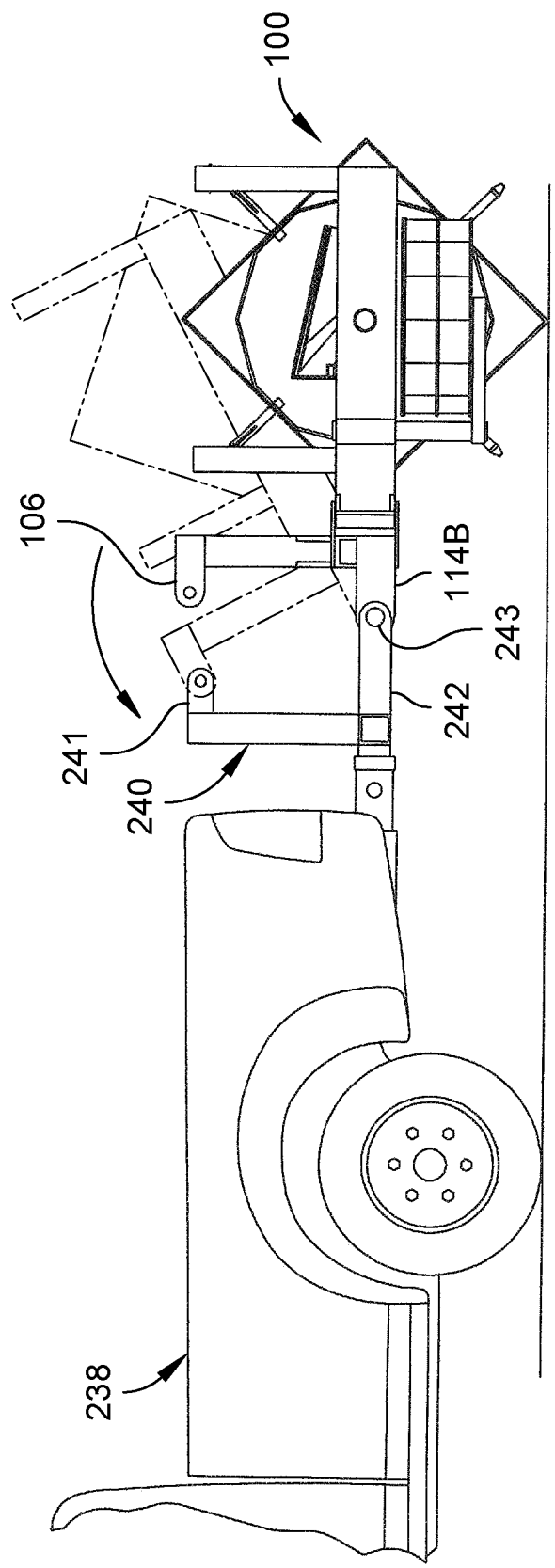
FIG. 12 is a side view illustrating the soil probe assembly of FIG. 1 coupled to a passenger vehicle.

In embodiments, assembly 100 is configured to couple to a vehicle. For example, in FIG. 11, assembly 100 is coupled to tractor 236 which has 3-point hitch linkages 226 and 227 (a third linkage is obscured from view). In another example, in FIG. 12, assembly 100 is coupled to passenger vehicle 238 which has 3-point hitch 240, wherein 3-point hitch 240 has members 240 and 242. During soil collection, assembly 100 is coupled to member 242 using pin 243, wherein pin 243 couples to at least bracket 114B (bracket 114A is obscured from view). When it is desired for assembly 100 to not collect soil samples, a user may couple bracket 106 to bracket 241 of member 240 with a corresponding pin (not shown), thereby raising assembly 100 off the ground and preventing the one or more soil probes from collecting soil samples.

Figure 13:
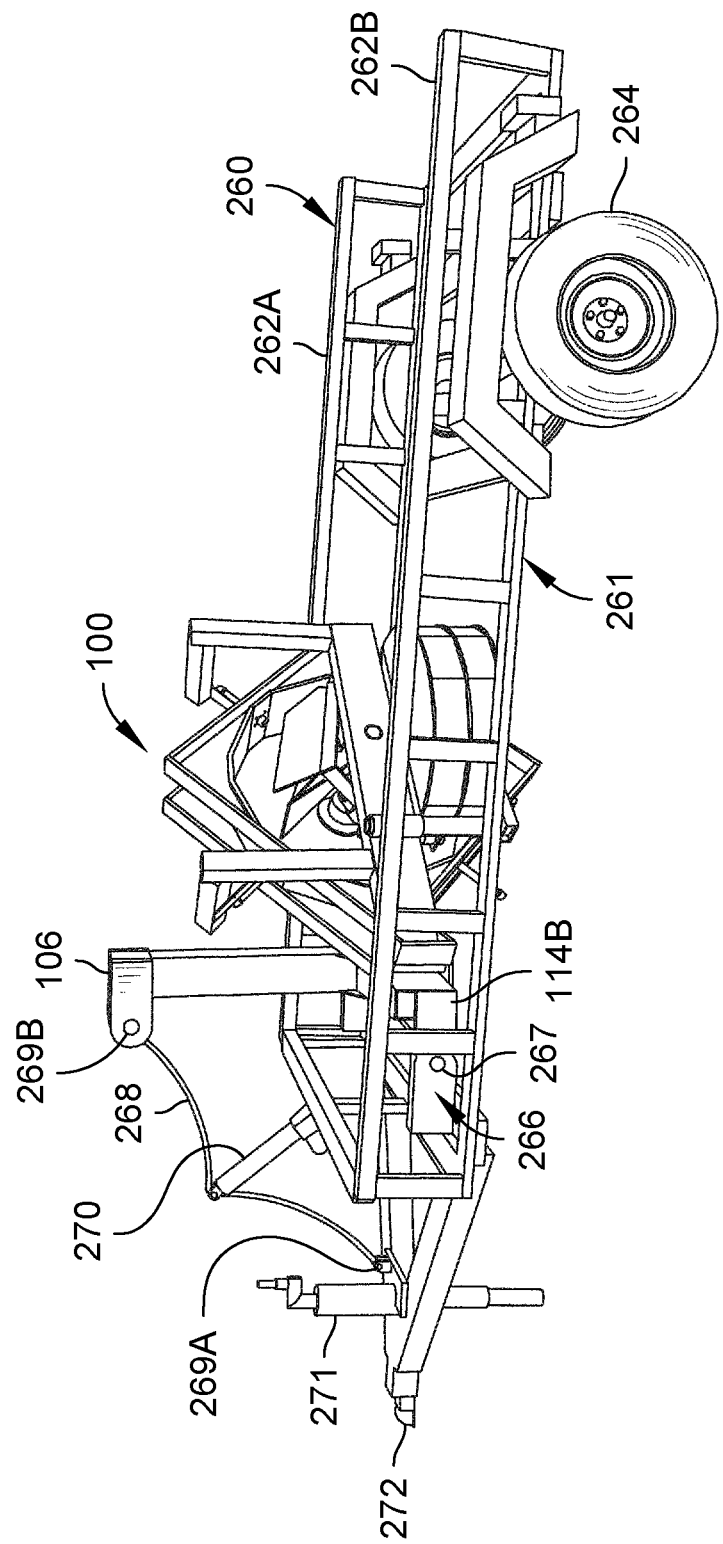
FIG. 13 is a perspective view illustrating a trailer configured to tow a soil probe assembly, such as the soil probe assembly of FIG. 1, in accordance with an example embodiment of the present disclosure.

In an embodiment, assembly 100 may couple to a trailer configured to house assembly 100, wherein the trailer is further configured to couple to a vehicle and further configured to permit assembly 100 to collect soil samples while housed by the trailer. For example, in FIG. 13, trailer 260 is depicted as housing assembly 100. Trailer 260 includes frame 261 which have opposing frame walls 262A and 262B, wheels 264, one or more mounting brackets (e.g., mounting bracket 266), jack screw 271 for supporting the weight of trailer 260 while trailer 260 is not in tow, hitch 272 configured to couple to a hitch of a vehicle, jack screw 270, and cable 268 having ends 269A and 269B. In this example, assembly 100 is located between frame walls 262A and 262B. Assembly 100 is coupled to trailer 260 by coupling brackets 114A (obscured from view) and 114B to the one or more mounting brackets of trailer 260 using a corresponding pin (e.g., coupling bracket 114B to mounting bracket 266 using pin 267). Furthermore, cable 268 couples bracket 106 of assembly 100 to trailer 260, wherein end 269B is coupled to bracket 106 and end 269A is coupled to trailer 260. To prevent assembly 100 from collecting soil samples, jack screw 270 is coupled between ends 269A and 269B of cable 268, wherein extending jack screw 270 against cable 268 causes tension in cable 268 and subsequently causes assembly 100 to pivot about pin 267 with respect to trailer 260.

Figure 14:
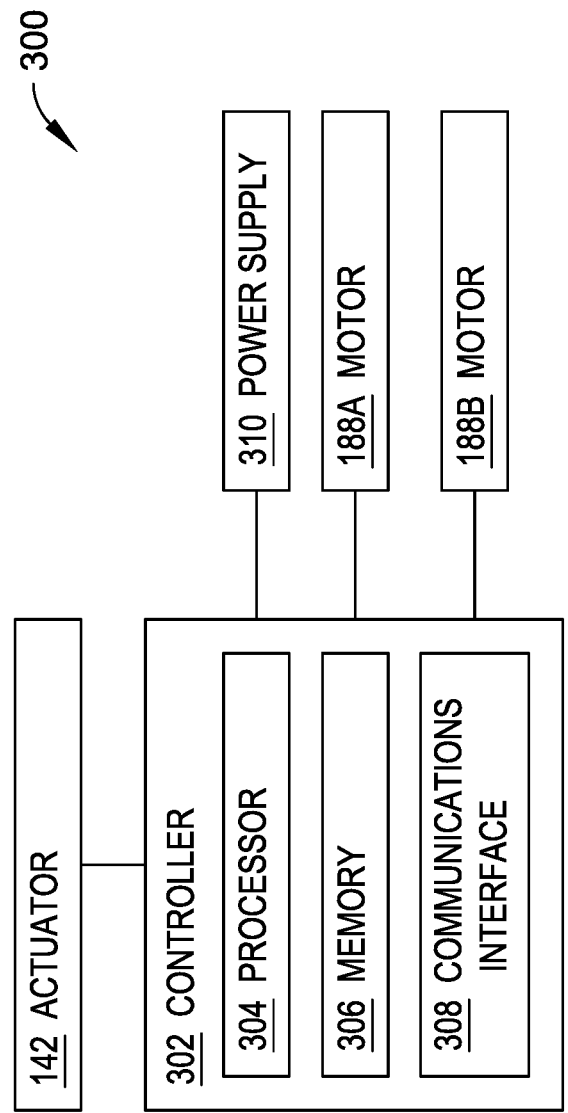
FIG. 14 is a functional block diagram illustrating a system including a set of motors for driving a corresponding set of carousels, an actuator for driving a funnel shield, and a controller for operating the set of motors and the actuator in accordance with an example embodiment of the present disclosure.

Referring now to FIG. 14, a system 300, including some or all of its components, can operate under computer control. For example, processor 304 can be included with or in system 300 to control the components and functions of system 300 described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the system 300. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

In general, controller 302 controls power supplied to actuator 142 and the one or more motors (e.g., motor 188A and 188B), wherein the power is supplied by power supply 310. The controller 302 can include processor 304, a memory 306, and a communications interface 308. Processor 304 provides processing functionality for the controller 302 and can include any number of processors, microcontrollers, or other processing systems, and resident or external memory for storing data and other information accessed or generated by controller 302. Processor 304 can execute one or more software programs that implement techniques described herein. The processor 304 is not limited by the materials from which it is formed or the processing mechanisms employed therein and, as such, can be implemented via semiconductor(s) and/or transistors (e.g., using electronic integrated circuit (IC) components), and so forth.

System 300 includes a memory 306. Memory 306 is an example of tangible, computer-readable storage medium that provides storage functionality to store various data associated with operation of system 300, such as software programs and/or code segments, or other data to instruct the processor 304, and possibly other components of the system 300, to perform the functionality described herein. Thus, the memory 306 can store data, such as a program of instructions for operating system 300 (including its components), and so forth. It should be noted that while a single memory 306 is described, a wide variety of types and combinations of memory (e.g., tangible, non-transitory memory) can be employed. The memory 306 can be integral with the processor 306, can comprise stand-alone memory, or can be a combination of both.

The memory 306 can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the system 300 or the memory 306 can include removable integrated circuit card (ICC) memory, such as memory provided by a subscriber identity module (SIM) card, a universal subscriber identity module (USIM) card, a universal integrated circuit card (UICC), and so on.

The system 300 includes a communications interface 308. The communications interface 308 is operatively configured to communicate with components of the system 300. For example, the communications interface 308 can be configured to transmit data for storage in the system 300, retrieve data from storage in the system 300, and so forth. The communications interface 308 is also communicatively coupled with the processor 304 to facilitate data transfer between components of the system 300 and the processor 304 (e.g., for communicating inputs to the processor 304 received from a device communicatively coupled with the system 300). It should be noted that while the communications interface 308 is described as a component of a system 300, one or more components of the communications interface 308 can be implemented as external components communicatively coupled to the system 300 via a wired and/or wireless connection. The system 300 can also comprise and/or connect to one or more input/output (I/O) devices (e.g., via the communications interface 154/communications interface 156), including, but not necessarily limited to: a display, a mouse, a touchpad, a keyboard, and so on.

The communications interface 308 and/or the processor 304 can be configured to communicate with a variety of different networks, including, but not necessarily limited to: a wide-area cellular telephone network, such as a 3G cellular network, a 4G cellular network, a 5G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to limit the present disclosure. Further, the communications interface 308 can be configured to communicate with a single network or multiple networks across different access points.

In implementations, a variety of analytical devices can make use of the structures, techniques, approaches, and so on described herein. Thus, although systems 300 are described herein, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

Generally, any of the functions described herein can be implemented using hardware (e.g., fixed logic circuitry such as integrated circuits), software, firmware, manual processing, or a combination thereof. Thus, the blocks discussed in the above disclosure generally represent hardware (e.g., fixed logic circuitry such as integrated circuits), software, firmware, or a combination thereof. In the instance of a hardware configuration, the various blocks discussed in the above disclosure may be implemented as integrated circuits along with other functionality. Such integrated circuits may include all of the functions of a given block, system, or circuit, or a portion of the functions of the block, system, or circuit. Further, elements of the blocks, systems, or circuits may be implemented across multiple integrated circuits. Such integrated circuits may comprise various integrated circuits, including, but not necessarily limited to: a monolithic integrated circuit, a flip chip integrated circuit, a multichip module integrated circuit, and/or a mixed signal integrated circuit. In the instance of a software implementation, the various blocks discussed in the above disclosure represent executable instructions (e.g., program code) that perform specified tasks when executed on a processor. These executable instructions can be stored in one or more tangible computer readable media. In some such instances, the entire system, block, or circuit may be implemented using its software or firmware equivalent. In other instances, one part of a given system, block, or circuit may be implemented in software or firmware, while other parts are implemented in hardware.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A soil probe assembly for collecting soil samples, comprising:
   a frame member;
   a wheel coupled to the frame member, the wheel configured to rotate with respect to an axis, the wheel including a tubular soil probe, the soil probe including an extraction opening and an ejection opening, the soil probe configured to receive a soil sample at the extraction opening and configured to release the soil sample from the ejection opening;
   a funnel coupled to the frame member, the funnel having a collection opening and a delivery opening, the collection opening being proximate to the ejection opening, the funnel configured to receive the soil sample at the collection opening and configured to release the soil sample from the delivery opening; and
   a carousel rotatably coupled to the frame member, the carousel configured to be selectively positioned about an axis of the carousel, the carousel including a bypass defined by the carousel, the bypass configured to permit the soil sample to pass through the bypass without capture by the carousel when the bypass is selected to receive the soil sample.

2. The assembly of claim 1, further comprising at least one collection hamper configured to receive the soil sample released by the funnel.

3. The assembly of claim 1, further comprising a second carousel rotatably coupled to the frame member, the second carousel configured to selectively position about the axis of the carousel, the second carousel configured to receive the soil sample from the bypass of the carousel.

4. The assembly of claim 3, further comprising at least one collection hamper configured to receive the soil sample from the bypass of the carousel.

5. The assembly of claim 3, the second carousel further comprising a bypass defined by the second carousel, the bypass of the second carousel configured to selectively permit the soil sample to pass through the bypass of the second carousel without capture by the second carousel based on the selected position of the second carousel.

6. The assembly of claim 1, further comprising a funnel shield, the funnel shield configured to selectively cover the collection opening of the funnel thereby prohibiting the soil sample from entering the funnel.

* * * * *